Figure 1:
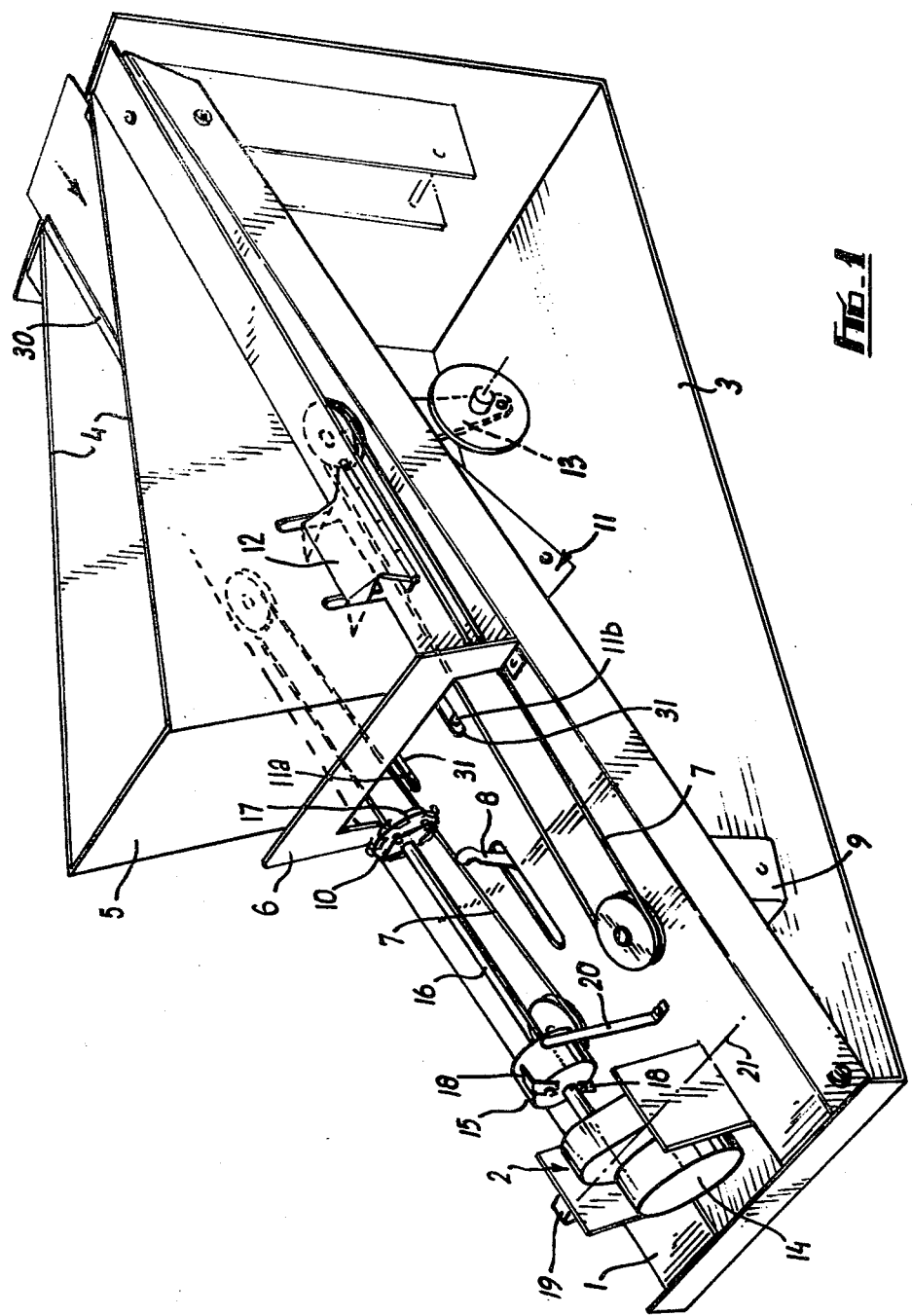

United States Patent [19]

Sequeira

[11] 4,144,135

[45] Mar. 13, 1979

[54] SPREADER DEVICE AND METHOD OF SPREADING INOCULANT

[75] Inventor: Peter J. L. Sequeira, Wilmslow, England

[73] Assignee: MPJ Developments Limited, London, England

[21] Appl. No.: 817,273

[22] Filed: Jul. 20, 1977

[30] Foreign Application Priority Data

Jul. 31, 1976 [GB] United Kingdom ............... 32036/76

[51] Int. Cl.² ........................... C12B 1/02; C12K 1/04
[52] U.S. Cl. ...................................... 195/120; 195/127
[58] Field of Search .................................. 195/127, 120

[56] References Cited

U.S. PATENT DOCUMENTS

| | | | |
|---|---|---|---|
| 3,455,788 | 7/1969 | Curry et al. ...................... | 195/120 X |
| 3,742,187 | 6/1973 | Folus ................................ | 195/127 X |
| 3,775,256 | 11/1973 | Risinger ........................... | 195/127 X |
| 3,778,351 | 12/1973 | Rosov .............................. | 195/127 |
| 3,788,951 | 1/1974 | Von Der Pfordten ............. | 195/120 |
| 3,799,844 | 3/1974 | Campbell et al. ................. | 195/127 |
| 3,830,701 | 8/1974 | Stussman et al. .................. | 195/120 |
| 3,841,973 | 10/1974 | Wilkins et al. .................... | 195/127 |
| 3,850,754 | 11/1974 | Wilkins et al. .................... | 195/127 |
| 3,935,075 | 1/1976 | Perry et al. ........................ | 195/127 |
| 4,010,077 | 3/1977 | Pardos .............................. | 195/120 X |

OTHER PUBLICATIONS

R. E. Trotman, Journal of Applied Bacteriology; vol. 34, No. 3, pp. 615–619; 1971.

L. S. Gall et al., Development in Industrial Microbiology, vol. 11, pp. 460–469; 1970.

Primary Examiner—Raymond N. Jones
Assistant Examiner—Robert J. Warden
Attorney, Agent, or Firm—Alan H. Levine

[57] ABSTRACT

A culture plate is fed down a ramp to a processing position rotated in that position and from that position moved up the ramp at a controlled rate while an innoculant spreader head is automatically brought into contact with the surface of the plate in order to produce a spiral form innoculant trace on the plate. The spreader head is subsequently automatically lifted from the plate and the plate automatically stacked. Movement up the ramp may be controlled by a cam operated arm extending up through the ramp or by differentially speed driven belts between which the plate is disposed.

15 Claims, 3 Drawing Figures

SPREADER DEVICE AND METHOD OF SPREADING INOCULANT

The present invention relates to method of and apparatus for spreading inocula on bacterial culture plates or like for procedures.

Conventionally, after a culture plate is inoculated, the inoculum is spread over the surface of the plate by rubbing the surface of the plate and part of the area of the inoculum with a sterilized wire loop. Further dilution of the inoculum is usually achieved by repeating the above procedure one or more times using a further loop, another portion of a large loop, or the same loop after being re-sterilized, spreading a further part of the surface of the plate using part of the surface already spread as a source of inoculum. The procedure is slow and exacting and devices to assist with the process include simple turntables and large free standing machines which automatically spread and stack a batch of plates.

According to one aspect of the present invention there is provided apparatus for spreading a culture plate with inoculant comprising mens for feeding a culture plate to be processed to and from a processing position, a spreader at the processing position and driving means for bringing the spreader into contact with the plate to produce a progressively more dilute inoculant trace thereon.

A preferred embodiment of the above aspect of the invention may comprise any one or more of the following features:

(a) The means for feeding comprises a single endless driving belt.

(b) The means for feeding comprises two spaced endless driving belts disposed on opposite sides respectively of the culture plate feed path to the processing position.

(c) The or each driving belt extends between two pulleys and means for driving one of each pair of pulleys is provided.

(d) The or each driving belt is made of rubber other suitable flexible friction material.

(e) The spreader comprises a number of component loops arranged in a substantially circular formation and disposed so that the loops can be sequentially brought into contact with the surface of the culture plate.

(f) The spreader of (e) is mounted for rotation about an axis through the plane of the circular formation.

(g) The spreader is made of an electrically conductive material and means are provided for enabling electrical current to be fed thereto to heat up the spreader and sterilize it.

(h) The means for feeding comprise a ramp sloping down to the processing position, a support enabling culture plates processed to be stacked one on top of the other, and a guide for removing a culture plate lid as the plate is fed to the processing position and for replacing the lid after processing has taken place.

(i) Control means are provided for controlling the actions of the means for feeding and the spreader in accordance with a predetermined sequence.

According to another aspect of the present invention, there is provided a method of producing a trace of inocula of progressive dilution weakness on a culture plate including the steps of depositing inocula on a plate, feeding the plate to a processing area, bringing a spreader into contact with the plate whilst moving the plate in relation thereto to produce an inocula trace on the plate and removing the processed plate from the processing area to a collection point.

The invention also comprises a culture plate when processed by the above method.

Figure 2:
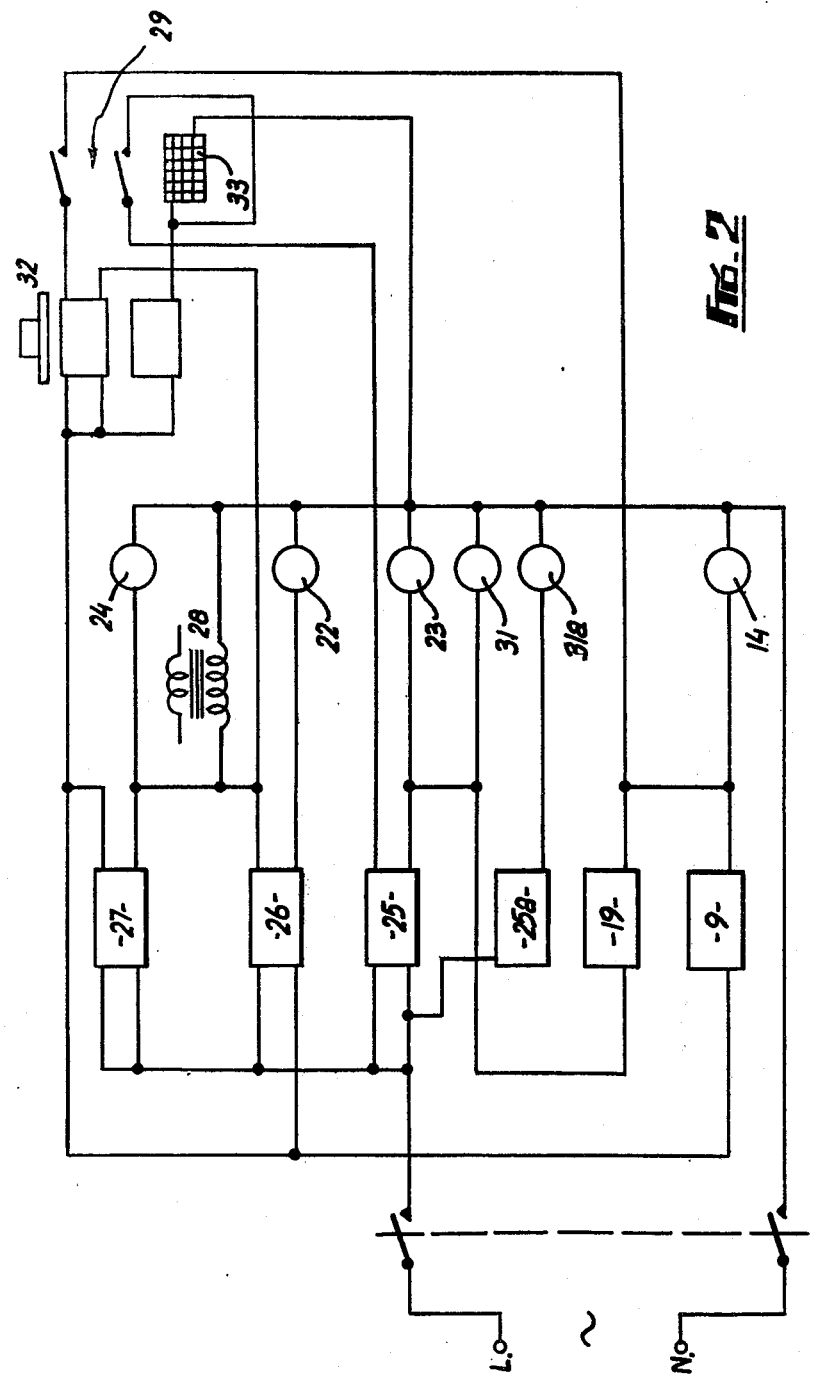
Figure 3:
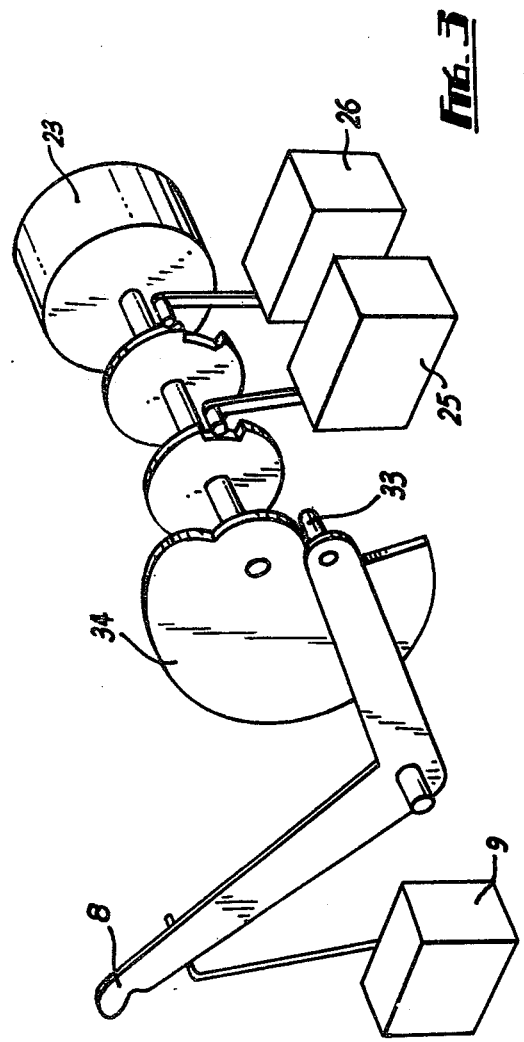

In order that the invention may be more clearly understood, one embodiment of the invention will now be described, by way of example, with reference to the accompanying drawings in which:

FIG. 1 shows a perspective view of inocula spreading apparatus with certain structural and control parts omitted for clarity, FIG. 2 shows a block circuit diagram of a control system for the apparatus of FIG. 1, and FIG. 3 shows a diagrammatic representation of the control mechanism.

Referring to FIG. 1, the apparatus may be considered as comprising three basic sections, namely a plate handling system based on an inclined plane 1, a spreader assembly 2, and a drive and control system (not wholly shown) which may conveniently be accommodated between a base 3 of the apparatus and the inclined plane 1.

The slope of the inclined plane 1 is such that a culture plate, which comprises a circular base and a circular detachable cover of slightly larger diameter, placed on it will slide down the inclined plane under the influence of gravity. Lateral movement of the culture plates is controlled by vertical surfaces 4 which are spaced apart at a distance slightly greater than the diameter of the plate cover.

The vertical surfaces 4 are joined by a plate 5 forming a receptacle for plates which have been processed or spread. The plate 5 is raised above the inclined plane 1 by supports 6 leaving sufficient space below the plate 5 for the base of the culture plate to pass beneath the plate 5.

The lower edges of the vertical surfaces 4 each carry an inward pointing shelf 30 spaced apart by a distance greater than the diameter of the plate base but less than the diameter of the plate cover. When a culture plate is placed (cover upwards) on the upper part of the inclined plane 1, the plate slides down the inclined plane 1 between the vertical surfaces 4 under gravity. The plate cover engages the above mentioned shelves 30, allowing the plate base to disengage from the cover which comes to rest when it reaches the plate 5.

At about the point where the plate base is disengaged from the cover, the plate base is caught between two spaced endless belts 7. One belt, (hereinafter referred to as the down belt) is in motion when the machine is not operating while the other belt (hereinafter referred to as the up belt) is stationary.

The motion of the down belt rolls the plate base down the up belt engaging a trigger 8 extending through a slot in the inclined plane 1 thus operating a switch 9 which initiates an operating cycle as hereinafter described. The slot through which the trigger 8 extends is disposed in the processing area and above this area a spreader comprising a spreader head 10 on the end of a speader shaft 16 extends. On initiation of the operating cycle the spreader head 10 is lowered onto the surface of the culture plate and the up belt starts moving in the opposite direction to the down belt. The relative motions of the belts causes the plate base to rotate. Small differences in the relative speeds of the belts will cause the plate base to move up or down the inclined plane, as the case may be.

In the preferred form of the invention, the plate base is caused to make about two rotations with the spreader close to the periphery, and then, still rotating, to move slowly up the inclined plane until the centre of the surface of the plate base reaches the spreader, hence spreading inoculum over the whole plate surface.

The spreader head 10 is then raised from the plate and the down belt stopped. The continuing action of the up belt rolls the plate base up the down belt until the plate base engages the cover retained on the above mentioned shelves 30 and plate 5. The plate base is raised into the cover, and plate and cover raised above two pawls 12 extending from respective surfaces 4 by a stacker 11. This stacker 11 comprises a pivotally mounted member having two upstanding extensions 11a and 11b aligned with two slots 31 formed in the inclined plane 1. When the stacker 11 is operated the extensions project through the slot 31 and lift the plate base into the plate cover and then past the pivotal pawls 12. On retraction of the stacker extensions the plate is lowered on the pawls which have in the meantime pivoted back to their rest position. Any culture plates already processed are displaced upwards in the channel formed by the vertical members 4 and plate 5. On withdrawal of the extensions below the inclined plane 1 the down belt is restarted, the up belt being stopped.

The operation is repeated when another culture plate is placed on the inclined plane 1. If the spreading and stacking operation of the previous culture plate is incomplete when another culture plate is placed on the inclined plane 1, it is arrested by the cover of the preceding culture plate, or by the stacker, until the stacker is withdrawn, and the process as described above is repeated. The dimensions of the upper part of the inclined plane are such as to accommodate a convenient number of culture plates awaiting spreading or processing.

The spreader includes a drive assembly which consists of a geared motor 14 carrying a slip-ring or commutator 15 on its output shaft. The shaft 16 is connected to the commutator 15 and carries on its end the spreader head 10 which consists of a mounting carrying two multiple loop spreaders, one of which is shown at 17.

The commutator or slip-ring 15 carries two cam surfaces 18, corresponding to respective multiple loop spreaders 17. When a cam surface 18 engages with the actuator of a switch 19, the spreader is tilted, raising the spreader head 10 from the culture plate or inclined plane 1. This motion is limited by a stop, and the switch 19 opens. A leaf-spring 20, vertically disposed to the inclined plane 1, presses tangentially on the slip-ring or commutator 15.

When the spreader head 10 is raised as described above, and the motor 14 is started, a cam surface 18 disengages from the actuator of switch 19, the spreader head is lowered onto a culture plate or the inclined plane 1 by the slip-ring or commutator 15 rolling down the leaf-spring 20, tilting the spreader assembly about a horizontal axis 21. The action of the leaf-spring 20 also damps the motion of the spreader assembly.

Each multiple loop spreader 17 consists of a length of suitable wire or the like formed into a series of loops, one side of each is straightened and disposed approximately parallel to the axis of spindle of the motor 14, and adjusted so that the straight sections are, in turn, in contact with the surface of the culture plate.

The relative direction of rotation of the culture plate and the spreader head is such that each successive straight section of the multiple spreader comes in contact with a portion of the plate just spread by the preceding straight section providing progressive dilution of the inoculum as in the conventional manual spreading procedure, but disposed in a spiral track rather than in different sectors of the plate surface.

The drive and control system co-ordinates the operations described above. By way of illustration, the control system will be described using a separate motor for each motion and two multiple spreaders. If desired, more than one motion could be driven from one motor by use of clutches or the like, using a similar logic of operation.

Referring to FIGS. 2 and 3, in the example described, the up and down belts are driven by identical constant speed motors 31 and 22 respectively. Motor 23 drives a series of cams operating two normal closed and two or three normal open switches 25, 25a and 26. The preferred compound radial movement of the plate base under the spreader may be obtained by driving the up belt slower than the down belt so that the plate base is held in its lowest position while the periphery of the plate is spread with inoculum. Then the plate base is moved up the inclined plane either by a spiral or other form cam 34 mounted on the shaft of motor 23 co-operating with a cam follower 33 connected with the trigger arm 8 which is moved up the slot, or by providing an additional drive motor 31a controlled by switch 25a, driving the up belt faster than the down belt.

The cycle time of the timer is the same as that which motor 14 takes to rotate the spreader head through the angle occupied by one multiple loop spreader.

The operation of the motor 24 for the stacker is controlled by a cam or the like on the stacker motor shaft which operates a stacker switch 27 through a small angle of rotation at the rest position. The motor 24 also carries a crank or the like which raises the extensions of the stacker 11 through the slot 31 in the inclined plane 1.

In the description below "normally closed" will be used to refer to contacts which are closed when the apparatus is in the resting position and "normally open" for contacts which are open in the resting position.

The electrical supply is taken to the feed contacts of normally closed and normally open switches of the stacker switch 27, the normally open pole of switch 26 and the supply poles of switch 25. The normally closed pole switch 26 and the trigger switch 9 are supplied from the normally closed contacts of the stacker switch 27.

When an incoming culture plate operates the trigger switch 9, the spreader motor 14 commences to rotate, disengaging the engaged cam surface 18 from the actuator of switch 19, allowing the spreader head to be lowered onto the culture plate and the switch 19 to close.

Closing of switch 19 starts the rotation of the "up belt" drive motor 31 and the cam motor 23, and the latter causes switch 25 to change over. The cam motor 23 and "up belt" drive motor 31 are now supplied through the normally closed contacts of switch 27 and the normally open contacts of switch 25. This supply also reaches the spreader motor 14 through switch 19 when the above mentioned movement of the culture plate up the inclined plane 1 causes the trigger switch 9 to open.

The spreading operation described above continues until the spreader head is raised from the culture plate by the reaction of a cam surface 18 on the actuator of switch 19, this causing switch 19 to open, and the spreader motor 14 to stop.

Switch 26 now changes over, causing the "down belt" drive motor to stop, ejecting the culture plate as described above, and simultaneously starting the stacker motor 24. Switch 27 changes over, supplying the stacker until it has completed its cycle.

A transformer 28 is connected in parallel with the stacker motor 24. The low voltage output from the secondary winding of the transformer is fed to the multiple loop spreader which has just been raised from the culture plate, heating it to incandescence to sterilize it.

The current from the transformer may be fed, for example, through the leaf-spring 20, and then through the slip-ring or commutator 15, and thence to the multiple loop spreader. The return might be through the cam surface 18 and the actuator of switch 19, or by dividing the slip-ring 18 into a commutator and disposing the stop for the motion of the spreader assembly above the commutator, and receives the return through the stop.

Initial sterilization of the multiple spreaders is provided by a 3-pole push switch 32 and the relay 29 which has two normally open contacts.

The two normally open contacts of the push switch 32 are supplied through the normally closed contact of switch 25.

One normally open contact of the push switch is connected to the relay coil 33, which when energized remains energised through one of the relay contacts.

Closing the other push switch contact supplies the stacker motor 24, initiating one cycle of the stacker, and sterilizing the multiple spreader last used. When the stacker cycle is completed, the closing of the normally closed contact of switch 27 energizes the spreader motor 14 via the normally closed contacts of the push switch, and the second relay contact, initiating a normal operating cycle, terminating in a stacker cycle, sterilizing the second multiple spreader.

When the above mentioned operating cycle results in the change-over of switch 25, supply to the relay 29 is discontinued, and the relay contacts open.

The above described apparatus is of relatively simple construction and small enough to stand on the laboratory bench where culture plates are inoculated, and spreads and stacks the culture plates faster than the techician can identify and inoculate the plates.

It will be appreciated that the above embodiment has been described by way of example and that many variations are possible without departing from the scope of the invention. In particular, although two multiple loop spreaders have been used, a single spreader or more than two spreaders may be used if desired. Furthermore, the two belt drive arrangement for the culture plates could be replaced by a single belt or other alternative arrangement. Advantageously, the or each belt is of flat or rectangular section.

Finally, although the invention has been described with particular reference to the spreading of inoculum on culture plates, it will have equal application in other fields where a similar spreading action is required.

What is claimed is:

1. Apparatus for spreading a culture plate with inoculant comprising means for feeding a culture plate to be processed to and from a processing position, a spreader at the processing position, and driving means for bringing the spreader into contact with the plate to produce a progressively more dilute inoculant trace thereon, said means for feeding comprising two spaced endless driving belts disposed on opposite sides, respectively of the culture plate feed path to the processing position and arranged for movement in opposite directions at the same or different speeds, whereby to produce translational and/or rotational movement of a culture plate disposed between them.

2. Apparatus as claimed in claim 1, in which two constant speed motors are provided for driving respective endless belts through respective pulleys in opposing directions whereby to rotate a culture plate disposed between them.

3. Apparatus as claimed in claim 2, in which each driving belt is made of rubber or other suitable flexible material.

4. Apparatus as claimed in claim 1, in which the spreader is made of an electrically conductive material and means are provided for enabling electrical current to be fed thereto to heat up the spreader to sterilize it.

5. Apparatus as claimed in claim 1, in which control means are provided for controlling the action of the means for feeding and the spreader in accordance with a predetermined sequence.

6. Apparatus as claimed in claim 1, in which the spreader comprises a spreader head, a motor for rotating the spreader head, a spreader actuating switch, and a mounting for the head enabling it to be rotated in dependence upon a cam surface from an inoperative position to an operative position when the spreader switch is actuated.

7. Apparatus as claimed in claim 6, wherein a trigger switch is disposed in the path leading to the processing position so that the spreader is automatically actuated by a plate on approaching the processing position.

8. Apparatus as claimed in claim 1, wherein the means for feeding a culture plate to and from the processing position comprises an arm disposed in the plate path leading to the processing position and operative to move a plate away from the processing position at a controlled rate.

9. Apparatus as claimed in claim 8, in which the controlled rate is determined by a motor driven cam and co-operating cam follower acting on the arm.

10. Apparatus as claimed in claim 1, in which means are provided associated with the two belts enabling them to be driven at different speeds to give a culture plate disposed between the belts a translational as well as a rotational motion.

11. Apparatus for spreading a culture plate with inoculant comprising means for feeding a culture plate to be processed to and from a processing position, a spreader at the processing position, and driving means for bringing the spreader into contact with the plate to produce a progressively more dilute inoculant trace thereon, said spreader comprising a plurality of component loops arranged around the periphery of a circle and disposed so that the loops can be sequentially brought into contact with the surface of the culture plate.

12. Apparatus as claimed in claim 11, in which the spreader is mounted for rotation about an axis through the plane of the circular formation.

13. Apparatus for spreading a culture plate with inoculant comprising means for feeding a culture plate to be processed to and from a processing position, a spreader at the processing position, and driving means for bringing the spreader into contact with the plate to produce a progressively more dilute inoculant trace thereon, said means for feeding comprising a ramp sloping down to the processing position, a support enabling processed culture plates to be stacked one on top of the other, and a guide comprising two guide members disposed on opposite sides, respectively, of the ramp and diverging therefrom for engaging the culture plate lid and removing it as the plate is fed to the processing position, retaining the lid while the culture plate base moves on to the processing position, and allowing the lid to be re-engaged by the base on its return journey from the processing position after processing has taken place.

14. Apparatus as claimed in claim 13, in which a stacker and a stacker motor for driving the stacker are provided, the stacker comprising a member movable from an inoperative position in which it lies below the ramp and an operative position in which it raises a plate to the support.

15. A method of producing a trace of inoculant of progressive dilution weakness on a culture plate including the steps of depositing inoculant on a plate, feeding the plate to a processing area by means of two spaced endless belts disposed on opposite sides, respectively, of the culture plate feed path to the processing position and moving in opposite directions at the same speed or different speeds so as to produce translational and/or rotational movement of the plate, bringing a spreader into contact with the plate whilst moving the plate in relation thereto to produce an inoculant trace on the plate, and removing the processed plate from the processing area to a collection point.

* * * * *